(12) United States Patent
Runyan

(10) Patent No.: US 7,972,263 B2
(45) Date of Patent: Jul. 5, 2011

(54) PENIS RIGIDITY STABILIZER AND METHOD THEREFOR

(76) Inventor: Donald Runyan, Yuma, AZ (US)

( * ) Notice: Subject to any disclaimer, the term of this patent is extended or adjusted under 35 U.S.C. 154(b) by 315 days.

(21) Appl. No.: 12/329,439

(22) Filed: Dec. 5, 2008

(65) Prior Publication Data

US 2010/0145141 A1    Jun. 10, 2010

(51) Int. Cl.
*A61F 5/00* (2006.01)

(52) U.S. Cl. .......................................................... 600/39

(58) Field of Classification Search .............. 600/38–41; 128/844

See application file for complete search history.

(56) References Cited

U.S. PATENT DOCUMENTS

| 3,401,687 | A | * | 9/1968 | Hood ............................. 600/39 |
| 4,182,319 | A | * | 1/1980 | Scott ............................. 600/39 |
| 4,863,449 | A | * | 9/1989 | Therriault et al. ............ 604/352 |
| 4,869,723 | A | * | 9/1989 | Harmon ........................ 604/349 |
| 5,509,891 | A | * | 4/1996 | DeRidder ...................... 600/39 |
| 5,513,654 | A | * | 5/1996 | Delson .......................... 128/844 |
| 5,623,945 | A | * | 4/1997 | Shecterle et al. ............. 128/842 |
| 6,182,661 | B1 | * | 2/2001 | Solanki et al. ................ 128/844 |

* cited by examiner

*Primary Examiner* — Samuel G Gilbert
(74) *Attorney, Agent, or Firm* — Jeffrey D. Moy; Weiss & Moy, P.C.

(57) ABSTRACT

A penis rigidity stabilizer and method therefore capable of being placed about the shaft of a penis while allowing the glans of the penis to remain exposed and capable of achieving and maintaining a rigid state and capable of maintaining its position about the shaft of the penis and being inherently rigid during sexual activity.

19 Claims, 2 Drawing Sheets

PENIS RIGIDITY STABILIZER AND METHOD THEREFOR

FIELD OF THE INVENTION

This invention relates generally to erection support devices and, more specifically, to an erection support device and method therefor having an open-cylindrical shape and having the ability to be extended over the shaft of a penis in order to maintain the shaft of a penis in an erect position while leaving the glans of the penis exposed.

BACKGROUND OF THE INVENTION

Erectile dysfunction is an inconvenience experienced by many. Medication to correct this issue has been increasingly prescribed in response to this problem. However, these different types of medications may have unwanted side effects or may be generally not recommendable for a given individual. Another possibility is that a person experiencing erectile dysfunction may not want to take medication to address the issue. Accordingly, it is beneficial to provide a simple mechanical device for achieving and maintaining an erection.

This invention addresses this issue by providing a sheath-like device having an opening for a penis at both ends and having walls capable of becoming longitudinally rigid and maintaining their rigidity during use, thus enabling a user to easily maintain an erection with a simple mechanical device and without the need for unwanted medication.

SUMMARY OF THE INVENTION

An object of the present invention is to provide a simple mechanical erectile aid capable of being easily placed on a penis and fitting snugly behind the glans of the penis and about the shaft of the penis, thereby functioning to keep the penis in a rigid state suitable for intercourse or other sexual activity despite the penis being at least partially flaccid.

Another object of the present invention is to provide a mechanical erectile aid that leaves the glans of the penis, where a large percentage of the sexual nerve endings are located, exposed, thereby allowing maximum contact with a large percentage of the user's sexual nerve endings and preventing unwanted interference with the user's sexual enjoyment.

A further and alternative object of the present invention is to provide a mechanical erectile aid capable of being easily placed on a penis that also functions as a condom.

BRIEF DESCRIPTION OF THE PREFERRED EMBODIMENTS

In accordance with one embodiment of the present invention, a penis rigidity stabilizer is disclosed, comprising, in combination, a substantially cylindrical tube having an inner wall, an outer wall, a first end defining a first opening, and a second end defining a second opening wherein the second end comprises a ridge being tapered to cause the second opening to be of a smaller diameter than the first opening, the substantially cylindrical tube conforming substantially to a shape of a corpus cavernosum of a penis when the substantially cylindrical tube being in an extended position, the first end being proximate the second end when the substantially cylindrical tube being in a retracted position, and at least one strip of material between the inner wall and the outer wall and between the first end and the second end, the material having sufficient rigidity to maintain the substantially cylindrical tube in a longitudinally extended position when the substantially cylindrical tube being in an extended position.

In accordance with another embodiment of the present invention, a method of maintaining an erection comprising the steps of providing a substantially cylindrical tube having an inner wall, an outer wall, a first end defining a first opening, and a second end defining a second opening wherein the second end comprises a ridge being tapered to cause the second opening to be of a smaller diameter than the first opening, the substantially cylindrical tube conforming substantially to a shape of a corpus cavernosum of a penis when the substantially cylindrical tube being in an extended position, the first end being proximate the second end when the substantially cylindrical tube being in a retracted position, providing at least one strip of material between the inner wall and the outer wall and between the first end and the second end, the material having sufficient rigidity to maintain the substantially cylindrical tube in a longitudinally extended position when the substantially cylindrical tube being in an extended position, sliding the first end and the second end of the substantially cylindrical tube over a glans of the penis so that the ridge of the second end being proximate a corona of the glans, and rolling the first end of the substantially cylindrical tube away from the second end of the substantially cylindrical tube and towards a bulb of the penis in order to maintain the corpus cavernosum of the penis in a substantially extended position.

In accordance with a further embodiment of the present invention, a penis rigidity stabilizer comprising, in combination, a substantially cylindrical tube having an inner wall, an outer wall, a first end defining a first opening, and a second end defining a second opening wherein the second end comprises a ridge being tapered to cause the second opening to be of a smaller diameter than the first opening, the substantially cylindrical tube conforming substantially to a shape of a corpus cavernosum of a penis when the substantially cylindrical tube being in an extended position, the first end being proximate the second end when the substantially cylindrical tube being in a retracted position, and at least one vinyl strip between the inner wall and the outer wall and between the first end and the second end, the vinyl strip having sufficient rigidity to maintain the substantially cylindrical tube in a longitudinally extended position when the substantially cylindrical tube being in an extended position.

The foregoing and other objects, features, and advantages of the invention will be apparent from the following, more particular description of the preferred embodiments of the invention, as illustrated in the accompanying drawings.

DETAILED DESCRIPTION OF THE PREFERRED EMBODIMENTS

Figure 1:
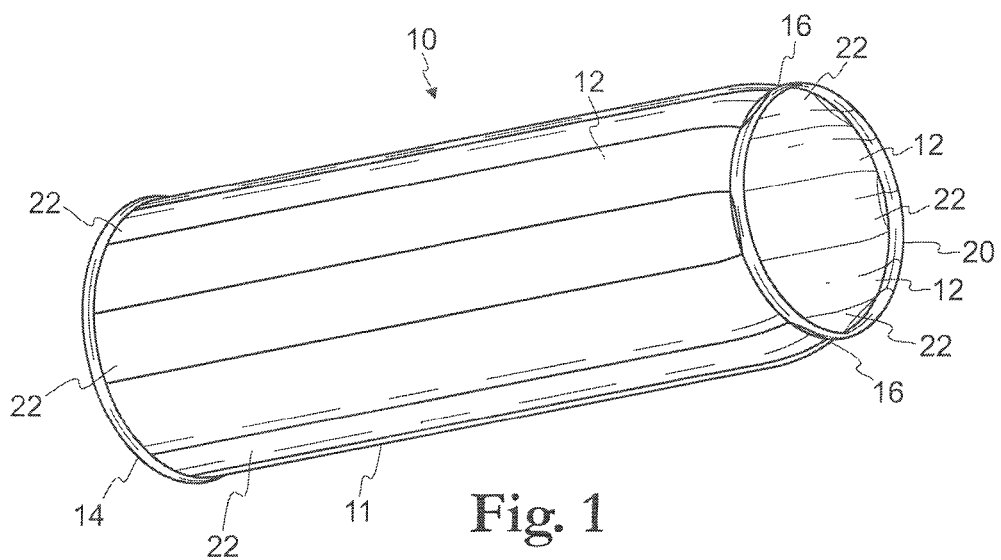
FIG. 1 is a perspective view of the penis rigidity stabilizer of the present invention in its extended position, showing a plurality of strips between the inner and outer walls of the penis rigidity stabilizer.
Figure 2:
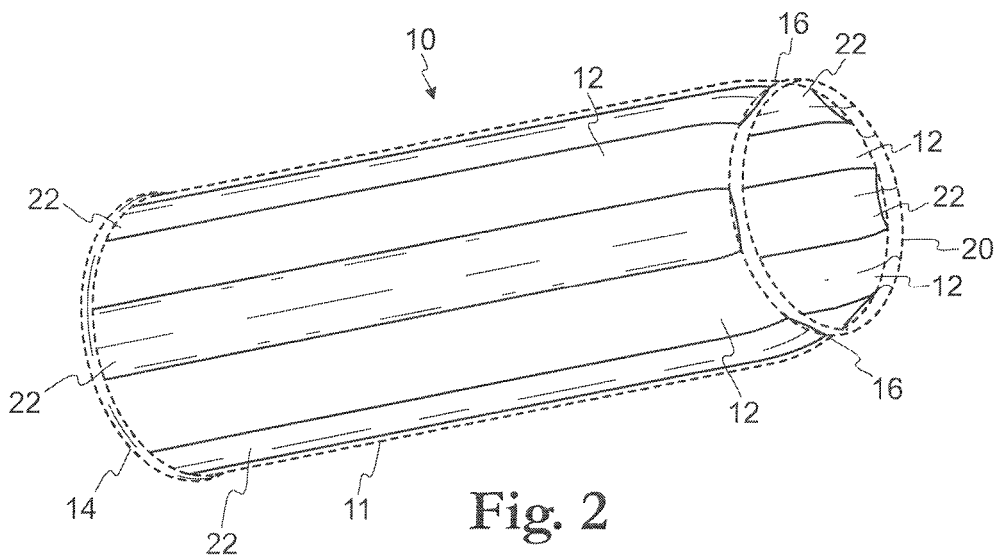
FIG. 2 is a perspective view of the penis rigidity stabilizer of FIG. 1, showing the walls of the penis rigidity stabilizer in phantom in order to better illustrate the details of the strips.

The novel features believed characteristic of the invention are set forth in the appended claims. The invention will best be understood by reference to the following detailed description of illustrated embodiments when read in conjunction with the accompanying drawings, wherein like reference numerals and symbols represent like elements.

Referring to FIGS. 1-4, various views of various states of a single embodiment of a penis rigidity stabilizer, referred to generically as the penis rigidity stabilizer 10, are disclosed. The penis rigidity stabilizer 10 comprises a substantially cylindrical tube 11, which is both hollow and open-ended. The substantially cylindrical tube 11 has walls 12 between a first end 14 a second end 16. The second end 16 forms a ridge 20. Preferably, the ridge 20 will be of a smaller circumference than the circumference of the first end 14, thereby causing the penis rigidity stabilizer 10 to follow, generally, the shape of a typical corpus cavernosum of a penis. The ridge 20 will enable the penis rigidity stabilizer 10 to fit snugly and securely behind the glans and on the sulcus of the penis, but it should be clear that substantial benefit is derived from alternative embodiments of the present invention wherein the penis rigidity stabilizer 10 is of different sizes and slightly different shapes in order to accommodate penises of various sizes and shapes.

Still referring to FIGS. 1-4, contained within the interior of the walls 12 of the penis rigidity stabilizer 10 is at least one strip of material, referred to generically as strips 22. The strips 22 have sufficient rigidity to maintain the substantially cylindrical tube 11 in a longitudinally extended position when the substantially cylindrical tube 11 is an extended position. Preferably, the strips 22 are long, thin, rigid but collapsible and made of vinyl, although it should be noted that substantial benefit is derived from alternative embodiments of the present invention wherein differing sizes and shapes of strips 22 are present and wherein the strips 22 are made of a material other than vinyl so long as the strips 22 are capable of maintaining the rigidity of the substantially cylindrical tube 11. In the preferred embodiment, the walls 12 themselves will be relatively smooth and will be composed of latex or another similar material, but it should be clear that substantial benefit is derived from an alternative embodiment of the present invention wherein the walls 12 are composed of a different material, or wherein the walls 12 are differently shaped or formed to give the walls 12 a different texture, such as ribbed or studded. In the preferred embodiment, the exterior of the inner surface of the walls 12 of the penis rigidity stabilizer 10 may be made of, or coated with, a material with a relatively high coefficient of friction to prevent movement of the penis rigidity stabilizer 10 with respect to the penis during use, though it should be clear that substantial benefit is derived from an alternative embodiment of the present invention in which the exterior of the inner surface of the walls 12 are not made of, or coated with, a material with a relatively high coefficient of friction.

Figure 3:
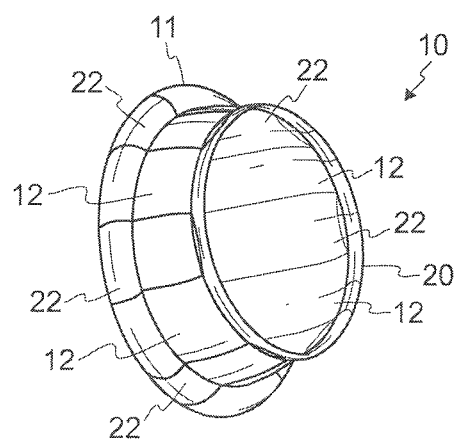
FIG. 3 is a perspective view of the penis rigidity stabilizer of FIG. 1 in a substantially retracted position.
Figure 4:
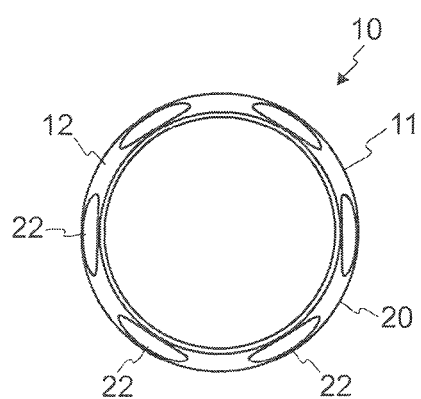
FIG. 4 is a front view of the penis rigidity stabilizer of FIG. 1 in its extended position, showing the strips within the walls of the penis rigidity stabilizer in their extended and rigid position and showing the ridge on the top end of the penis rigidity stabilizer at the forefront.

Referring now to FIGS. 3 and 4, the penis rigidity stabilizer 10 is shown in a substantially retracted position with the various strips 22 being individually collapsed within the walls 12 of the penis rigidity stabilizer 10. When the penis rigidity stabilizer 10 is made ready for use, the user places the glans through the penis rigidity stabilizer 10 in its retracted position with the second end 16 facing away from the user. The user then rests the ridge 20 of the second end 16 just behind the glans and then extends the penis rigidity stabilizer 10 until the various strips 22 are in an extended and rigid position, at which point the penis rigidity stabilizer 10 is ready for use.

Figure 5:
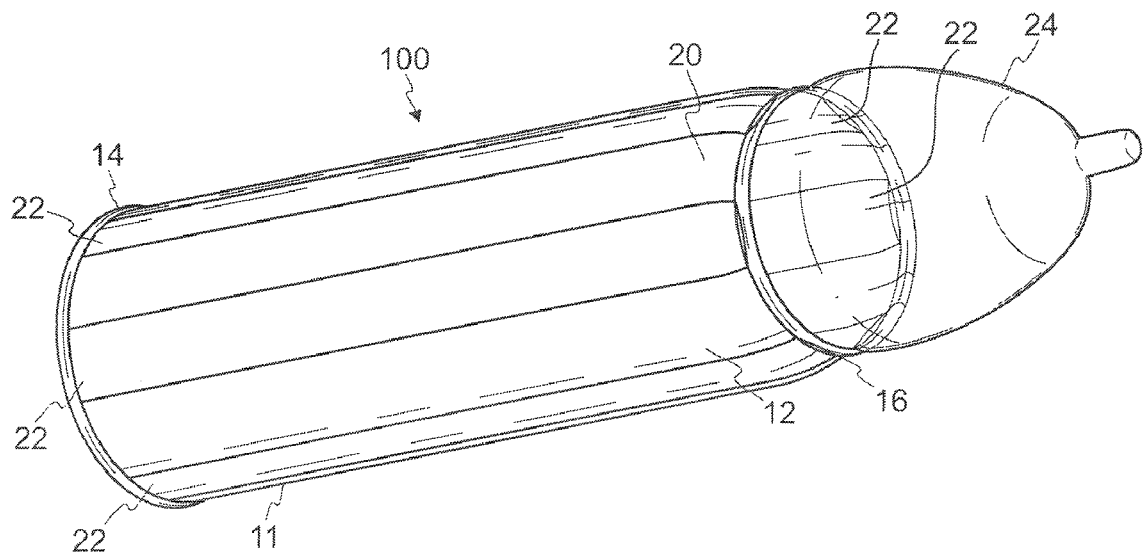
FIG. 5 is a perspective view of another embodiment of the penis rigidity stabilizer of the present invention in its extended position, showing a plurality of strips between the inner and outer walls of the penis rigidity stabilizer and showing a cover coupled to the end of the penis rigidity stabilizer and dimensioned to house a glans of a penis, thereby causing the penis rigidity stabilizer to also function as a condom.
Figure 6:
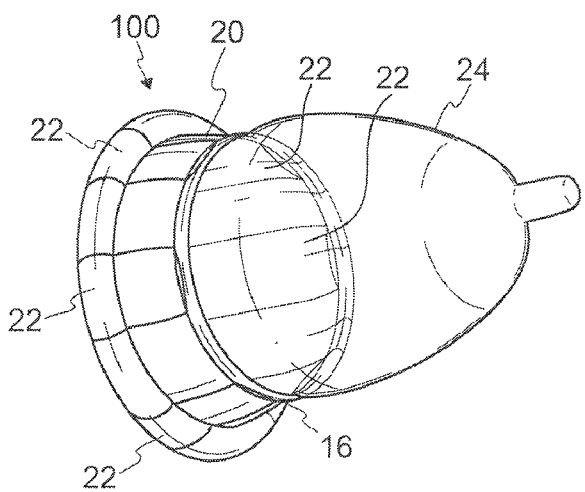
FIG. 6 is a perspective view of the penis rigidity stabilizer of FIG. 5, shown in a substantially retracted position.

Referring now to FIGS. 5 and 6, an alternative embodiment of the penis rigidity stabilizer 10, hereinafter referred to as the penis rigidity stabilizer 100, is shown. The penis rigidity stabilizer 100 is substantially the same as the penis rigidity stabilizer 10 except that the penis rigidity stabilizer 100 comprises a cover 24 coupled to the second end 16 of penis rigidity stabilizer 100. The cover 24 is dimensioned to house a glans of a penis, thereby causing the penis rigidity stabilizer to provide the additional functionality of a condom in addition to providing erectile assistance.

While the invention has been particularly shown and described with reference to preferred embodiments thereof, it will be understood by those skilled in the art that the foregoing and other changes in form and details may be made therein without departing from the spirit and scope of the invention.

I claim:

1. A penis rigidity stabilizer comprising, in combination:
   a substantially cylindrical tube having an inner wall, an outer wall, a first end defining a first opening, and a second end defining a second opening wherein said second end has a ridge formed thereon, said ridge used to secure said stabilizer behind a glans of a penis, the second opening being tapered to cause said second opening to be of a smaller diameter than said first opening, said substantially cylindrical tube conforming substantially to a shape of a corpus cavernosum of said penis when said substantially cylindrical tube being in an extended position, said first end being proximate said second end when said substantially cylindrical tube being in a retracted position; and
   at least one strip of material between said inner wail and said outer wall and between said first end and said second end, said material having sufficient rigidity to maintain said substantially cylindrical tube in a longitudinally extended position when said substantially cylindrical tube being in an extended position.

2. The penis rigidity stabilizer of claim 1 wherein said first end being at least one inch from said second end when said substantially cylindrical tube being in an extended position.

3. The penis rigidity stabilizer of claim 1 wherein said penis rigidity stabilizer being substantially ring shaped when said first end being proximate said second end when said substantially cylindrical tube being in a retracted position.

4. The penis rigidity stabilizer of claim 1 wherein said material of said at least one strip being vinyl.

5. The penis rigidity stabilizer of claim 1 wherein at least one of said inner wall and said outer wall being made of latex.

6. The penis rigidity stabilizer of claim 1 wherein said inner wall being one of made of a material and coated with a material having a sufficiently high coefficient of friction to prevent movement of said substantially cylindrical tube with respect to said penis during sexual activity.

7. The penis rigidity stabilizer of claim 1 wherein said at least one strip of material being made collapsible by self-coiling.

8. The penis rigidity stabilizer of claim 1 wherein said outer wall being textured so as to be at least one of studded and ribbed and dotted.

9. The penis rigidity stabilizer of claim 1 further comprising a cover coupled to one of said second end and said ridge and dimensioned to house said glans of said penis.

10. A method of maintaining an erection comprising the steps of:
   providing a substantially cylindrical tube having an inner wall, an outer wall, a first end defining a first opening, and a second end defining a second opening wherein said second end has a ridge formed thereon, said ridge used to secure said stabilizer behind a glans of a penis, the second opening being tapered to cause said second opening to be of a smaller diameter than said first opening, said substantially cylindrical tube conforming substantially to a shape of a corpus cavernosum of a penis when said substantially cylindrical tube being in an extended position, said first end being proximate said second end when said substantially cylindrical tube being in a retracted position;
   providing at least one strip of material between said inner wall and said outer wall and between said first end and said second end, said material having sufficient rigidity to maintain said substantially cylindrical tube in a longitudinally extended position when said substantially cylindrical tube being in an extended position;
   sliding said first end and said second end of said substantially cylindrical tube over a glans of said penis so that said ridge of said second end being proximate a corona of said glans; and
   rolling said first end of said substantially cylindrical tube away from said second end of said substantially cylindrical tube and towards a bulb of said penis in order to maintain said corpus cavernosum of said penis in a substantially extended position.

11. The method of claim 10 wherein said first end being at least one inch from said second end when said substantially cylindrical tube being in an extended position.

12. The method of claim 10 wherein said penis rigidity stabilizer being substantially ring shaped when said first end being proximate said second end when said substantially cylindrical tube being in a retracted position.

13. The method of claim 10 wherein said material of said at least one strip being vinyl.

14. The method of claim 10 wherein at least one of said inner wall and said outer wall being made of latex.

15. The method of claim 10 wherein said inner wall being one of made of a material and coated with a material having a sufficiently high coefficient of friction to prevent movement of said substantially cylindrical tube with respect to said penis during sexual activity.

16. The method of claim 10 wherein said at least one strip of material being made collapsible by self-coiling.

17. The method of claim 10 wherein said outer wall being textured so as to be at least one of studded and ribbed and dotted.

18. The method of claim 10 further comprising the step of providing a cover coupled to one of said second end and said ridge and dimensioned to house a glans of said penis.

19. A penis rigidity stabilizer comprising, in combination:
   a substantially cylindrical tube having an inner wall, an outer wall, a first end defining a first opening, and a second end defining a second opening wherein said second end has a ridge formed thereon, the ridge used to secure said stabilizer behind a glans of a penis, the second opening being tapered to cause said second opening to be of a smaller diameter than said first opening, said substantially cylindrical tube conforming substantially to a shape of a corpus cavernosum of a penis when said substantially cylindrical tube being in an extended position, said first end being proximate said second end when said substantially cylindrical tube being in a retracted position; and
   at least one vinyl strip between said inner wall and said outer wall and between said first end and said second end, said vinyl strip having sufficient rigidity to maintain said substantially cylindrical tube in a longitudinally extended position when said substantially cylindrical tube being in an extended position.

* * * * *